United States Patent [19]  [11] 3,940,381
Boissevain  [45] Feb. 24, 1976

[54] PHARMACEUTICALLY ACTIVE COMPOUNDS AND THEIR PREPARATION AND COMPOSITIONS

[76] Inventor: Laurens R. Boissevain, 8 rue Bel Respiro, Monte Carlo, Monaco

[22] Filed: Aug. 13, 1973

[21] Appl. No.: 387,822

[30] Foreign Application Priority Data
Aug. 22, 1972  United Kingdom............... 13455/72

[52] U.S. Cl.............................. 260/210 R; 424/180
[51] Int. Cl.². ........................................... C07G 3/00
[58] Field of Search....... 260/210 R, 210 AB, 209 R

[56] References Cited
UNITED STATES PATENTS
3,332,962  7/1967  Grayson et al.................. 260/210 R
3,359,169  12/1967  Slater et al...................... 260/210 R
3,629,231  12/1971  Hough et al. ................... 260/210 R Primary Examiner—Lewis Gotts
Assistant Examiner—Cary Owens
Attorney, Agent, or Firm—Lawrence Rosen; E. Janet Berry

[57] ABSTRACT

A product is described that is of value for treatment of, for example, gastric ulcer. It contains iron or glycyrrhizinate with most of the glycyrrhizinic moieties being insoluble in water. A method of making it, involving prolonged heating, and pharmaceutical compositions and methods, are also described.

6 Claims, No Drawings

PHARMACEUTICALLY ACTIVE COMPOUNDS AND THEIR PREPARATION AND COMPOSITIONS

It is well known that liquorice root is a source of material that has useful effect in the treatment of gastritis, gastric ulcer and duodenal ulcer. Unfortunately therapeutic agents derived by extraction of components of liquorice root tend to suffer from the disadvantage that they exhibit undesirable side effects. Liquorice contains glycyrrhizinic acid (referred to below as gza) which is the $\beta,\beta'$-glucoronic acid ester of glycyrrhetinic acid (referred to below as gta). Certain derivatives of glycyrrhetinic acid are widely used as therapeutic agents in the treatment of gastritis, gastric and duodenal ulcer but they do still suffer from a number of undesirable side effects inherent in liquorice root and liquorice, especially when administered during the relatively long periods necessary for the complete healing of ulcers. For example it is generally considered unwise to use derivatives of glycyrrhetinic acid, or other extracts of liquorice, for the treatment of elderly patients or patients with cardiovascular, renal or hepatic diseases. Further, I consider there is no convincing clinical proof as to the therapeutic value of gta derivatives in the treatment of duodenal ulcer.

Also, although the administration of known liquorice-derived preparations may sometimes result in the temporary betterment or disappearance of the ulcer the treatment appears primarily to bring relief owing to the antacid and spasmolytic qualities of such preparations rather than to their terapeutic effect. Thus although there may be temporary improvement, the ulcer is not completely healed and is liable to reoccur after a fairly short interval. Hospitalization and surgery are usually necessary in the long run. In fact the same sort of results can be expected from a placebo administered to ulcer patients, so that no therapeutic value can be ascribed to such preparations.

Various reasons have been given as to the cause of the undesirable side effects. In some instances at least it is proposed that these are due to the presence of glycyrrhizinic acid in liquorice, which forms glycyrrhetinic acid after administration, or to glycyrrhetinic acid.

Proposals have therefore been made to produce pharmaceutical compositions derived from liquorice root or reduced glycyrrhizinic acid content. For example in Canadian Pat. No. 576,605 a process is described that is intended to eliminate the gza (and also the gta) content of liquorice. In this liquorice root is heated in water, aniseed and ferrum reductum are added to the extract after cooling, the mixture is stirred for two hours and filtered and the filtrate dessicated in vacuum. The short treatment with ferrum reductum apparently causes most of the glycyrrhizinic acid to be precipitated out, and therefore removed by the filtration.

I have found that a material having valuable properties in the treatment of gastritis, gastric ulcer and duodenal ulcer and having hardly any or no undesirable side effects in one which is sparingly soluble in water and which contains at least 5% by weight glycyrrhizinic moieties. In this specification I use the words "sparingly soluble" to indicate that the product has a substantial content of insolubles and a small content of solubles, and preferably to indicate that not less than 0.05 (and preferably not less than 0.1) grams but not more than 5 grams (preferably not more than 2 grams) of the compound can be dissolved in 100 ml of water at 20°C. The sparingly soluble form is an iron or aluminium derivative of glycyrrhizinic acid.

The exact chemical nature of the product is uncertain but there is probably some intermolecular or intramolecular bonding. What is now clear is that the preferred product of the invention contains iron or aluminium glycyrrhizinate and has an amount of glycyrrhizinic moieties which is at least 5%, and preferably at least 10%, by weight and has at least two-thirds, preferably at least four-fifths, of the glycyrrhizinic moieties being insoluble in water. It is found that satisfactory products containing iron glycyrrhizinate generally have a weight ratio of iron to glycyrrhizinic moieties of between 1:10 and 1:25. The most satisfactory products have a weight ratio of approximately 1:18 (as is found for pure iron glycyrrhizinate). The glycyrrhizinic moiety weights are calculated as acid, i.e., as gza.

It is preferred that the product should contain soluble glycyrrhizinic moieties as well as insoluble moieties and normally from 1 to 33%, preferably 1 to 20%, by weight of the glycyrrhizinic moieties are soluble and 67 to 99%, preferably 80 to 99%, are insoluble. Preferably from 5 to 15% by weight are soluble and 85 to 95% are insoluble.

Preferred products contain from 1.5 to 2.5% by weight soluble glycyrrhizinic moieties (measured as acid) and 25 to 35% by weight insoluble materials, with the most satisfactory products generally containing from 1.5 to 2% of soluble glycyrrhizinic moieties and from 30 to 33% of insoluble materials.

These figures on solubility are the figures obtained by shaking 1 gram of the product with 50 ml of water, centrifuging and washing the undissolved residue three times with 50 ml of water, centrifuging and decanting each time, followed by freeing the aqueous solution from iron by passing hydrogen sulphide through it at a pH of 8.9, filtering the product, evaporating the filtrate, dissolving the product in 5% sulphuric acid and hydrolysing it by boiling for two hours to liberate gta which is then extracted with 20 ml chloroform and dried on anhydrous sodium sulphate for four hours and evaporated. Finally the residue is dissolved in 1 ml 1:1 chloroform:methanol and analysed semiquantitatively by thin layer chromatography against known amounts of pure gta. The analytical error in this method in the amount of glycyrrhizinic moiety solubles never exceeds 20% based on the amount determined.

The sparingly soluble product of the invention may be made by a process comprising heating the product containing water-soluble iron or aluminium glycyrrhizinate at a temperature of at least 70°C for a sufficient time for the solubility to be reduced to the desired amount.

The product that is heated in this process may be a solid, for example, a product that has been made by spray drying or otherwise evaporating a solution of the glycyrrhizinate, but most usually is itself a solution.

Thus the heating may be conducted during the evaporation of a soluble of the iron or aluminium glycyrrhizinate or during baking of solid iron or aluminium glycyrrhizinate, or both.

In one method a dilute solution, preferably containing from 0.05 to 5% most preferably 0.1 to 1%, for example 0.3%, by weight dissolved solids is evaporated by heating at a temperature above 70°C for a sufficient time for the concentration of the dissolved solids to increase to a value of at least 30% by weight, preferably at least 50% by weight, for example 70% by weight and the resultant syrup is finally dried at any convenient temperature. In another method the syrup is formed by any convenient evaporation method and is then dried for example, under vacuum, at the temperature above 70°C for a prolonged period. In a further method solid soluble iron or aluminium glycyrrhizinate is formed and is then baked at a temperature above 70°C for a prolonged period.

Any evaporation step may be conducted under vacuum but if temperatures above 70°C are maintained during evaporation it is generally desirable to keep the vacuum rather low as otherwise frothing can be a problem. In a preferred method of the invention dilute solution is added gradually to a vessel which is heated under atmospheric pressure or under low vacuum until the vessel is full of syrup having a concentration greater than 50% and the syrup is then heated for at least twelve hours at a temperature greater than 60° or 80°C after the last addition of solution has been made, and the product is finally dried in any convenient manner.

The duration of the heating above 70°C affects the solubility of the final product. If the duration is too short then inadequate solubility is imparted to it. Generally increasing the temperature permits one to conduct the heating for a shorter time. The temperature is preferably at least 80°C, usually 90°C or more. Normally it is below 140°C. The duration is generally 6 to 72 hours, preferably 18 to 48 hours. The best results are often obtained at 24 to 36 hours, especially when the temperature is from 100° to 120°C.

The content of the solution that is subjected to evaporation is important. The solution that is evaporated in the process described in Canadian Pat. No. 576,605 has dissolved in it substantially no iron glycyrrhizinate. I have had reproduced on my behalf the process described therein and analysis of the product shows that the total amount of glycyrrhizinic moieties is about 1% by weight. In the invention the proportion of total solids in the starting solution, and thus in the final product, that is glycyrrhizinic moieties is always at least 5%, and usually more. Thus generally it is at least 10% and may be at least 12% or preferably 14% or higher for example it is often about 20%. If the product of the invention is made from pure glycyrrhizinic acid then the amount will indeed be very much higher but it is generally found that best results are obtained when the product of the invention is made from liquorice, especially "succus liquiritiae," the product necessarily therefore containing various other components derived from liquorice.

The starting solution may best be prepared by extracting insoluble metal glycyrrhizinate over a prolonged period, for example at least 12 hours and usually more than 24 hours, with water. Thus active iron or aluminium may be included in an aqueous mixture obtained by extraction of liquorice, and which therefore contains some gza, and the mixture allowed to stand, with repeated stirring, for a prolonged period. It is believed that metal glycyrrhizinate first precipitates but redissolves in the mixture again during the prolonged digestion.

A convenient way of forming the aqueous digestion mixture containing glycyrrhizinic moieties and metal and precipitate is to form a suspension of liquorice solids in water and then to add to the suspension the active iron or aluminium.

Active iron or aluminium used in the invention may be any compound or form of iron or aluminium that will react with the system to give the desired salt formation such that the desired degree of insolubility is obtained on heating to a sufficient extent. Normally 0.2 to 5%, preferably 0.5 to 2%, of the weight of the non-aqueous components of the solution, and therefore of the final product, is iron or aluminium. Normally finely divided iron obtained by reduction with hydrogen is used, for example ferrum reductum, or powdered aluminium.

Digestion is continued for as long as is necessary to achieve adequate or complete digestion. It may be, for example, 2 to 3 or even 6 days and is usually at least 1 day. Preferably the mixture is stirred repeatedly or continuously throughout much of this period. The digestion is preferably conducted at at least room temperature. Preferably it is slightly above, for example 20° to 40°C, most preferably 30° to 40°C, e.g., 35°C. The slightly elevated temperature may be obtained by external heating or sufficient heat may be generated by the exothermic nature of the reaction or reactions that occur within the solution.

It is sometimes convenient to include an enzyme in the extraction liquor, for example ground coriander or other oil containing seed, for example linseed, cotton seed and corn seed. The inclusion of such an enzyme may serve as a convenient way of raising the temperature.

Before subjecting the aqueous solution resulting from the digestion step to the evaporation process it is preferred to remove all the solids from it. For example for at least the last day, and preferably 2 days, of the digestion the mixture may be unstirred and the supernatant liquid may then be filtered off or, more usually, decanted. The resultant liquid may again be left to stand, for example for 12 hours or more, preferably 1 day, and the supernatant liquid may again be decanted or filtered. The solids collected in each decanting operation may be washed, the resultant slurries being left to stand for several days before they too are decanted, the clear liquid being added to the clear liquid already collected. The temperature during the standing and decanting period may be about room temperature.

Pharmaceutical compositions according to the invention comprise the sparingly soluble product containing at least 5% glycyrrhizinic moieties and a pharmaceutically acceptable carrier.

The composition preferably includes also magnesium oxide, so that a better defaecation pattern, an improved blood circulation in the liver and an increase in the Mg content in the blood may be attained. These are all factors of importance in the treatment of gastric and duodenal ulcer. The composition may also include antacids, e.g., magnesium trisilicate which has a slow but prolonged antacid action, and known protective coatings such as bismuth subnitrate or sulphated polysaccharides.

The composition may be in any suitable form. For example it may be a suppository, the carrier then being a suppository support, for example gelatine rectal capsules. This is of particular value for treating internal hemorrhoids. The composition may be an injectable composition, the carrier then usually being or comprising a sterile liquid, e.g., water. The composition may be administered orally, for example the carrier being a liquid or particulate solid. Thus the composition may be in the form of ampoules or of a powder, tablets, pills or capsules and so forth. Also the composition may be administered topically, the carrier then comprising any suitable cream or other base for topical administration.

Although the compositions may include antacids and other active ingredients that may improve initial relief to the patient, it must be emphasized that antacids alone cannot bring about a therapeutic cure. Contrary to the general assumption that gastroduodenal ulcer is caused by hyperacidity, and should therefore be combatted by use of an antacid, I ascribe the onset of gastroduodenal ulcer to an inflammation of the intestinal tract, thus producing a disruption of the mucous membrane, and this suggests that proper medical treatment would require a non-toxic anti-inflammatory agent rather than an antacid. This non-microbial inflammation seems to be caused by malfunction of the autonomic nervous system and I believe that in addition to treating gastritis, which is a non-microbial infection, a wide variety of non-microbial inflammations having a psychosomatic origin may be cured by the use of the products of the invention. Thus in addition to curing gastritis, and gastric and duodenal ulcer I believe the product of the invention will also be useful in treating asthma bronchalis, essential hypertension, angina pectoris, primary chronic rheumatoid arthritis, certain skin diseases and ulcerative colitis.

In addition to having these required anti-inflammatory properties the product of the invention has a histiogenic effect, i.e., the ability to build tissue and thus cause regeneration of damaged tissue. This is extremely important.

The following are some examples of the invention.

EXAMPLE 1

In a vessel I of 10 L. a quantity of 1¼ kilogram liquorice powder is mixed with about 6 L. warm water and stirred to a visually homogeneous suspension. To this 74 g of ground coriander seed may be added and finally 100 g of active ferrum reductum is well mixed into the mixture which is then stirred at intervals over a period of 3 days while maintaining the mixture at least at room temperature. For example the temperature in the mixture may be 35°C. The mixture is then diluted with enough water to render it liquid enough to pour the whole contents into a vessel II of 20 L. in which a further quantity of water of some 10 L. is added.

The contents of vessel II is thereupon stirred 10 times at intervals of 20 minutes and thereafter allowed to stand during 2 days, so that it remains about 2½ days in vessel II. If froth has formed, this is eliminated; the clarified liquid is then transferred to a vessel III of 20 L. leaving the slurry in vessel II.

In vessel III the liquid is kept during one day and thereafter the clear liquid is transferred to vessel V, leaving one again a slurry in vessel III, but in a lesser amount that before.

The slurries which were left behind in vessels II and III can be collected as a matter of economy in a vessel IV and this remains standing up to some 7 days after they have been washed until a clear liquid results, which is added to the liquid in vessel V.

The clear liquid in vessel V undergoes a process of evaporation at a temperature increasing to 90°C until a syrupy brown concentrate with a moisture content of about 30% remains, the temperature being above 70°C for at least 24 hours. This concentrate is then dried under vacuum. The yield is around 300 g, when the liquorice powder used in the preparation has a glycyrrhizinic acid content of about 12%.

EXAMPLE 2

100 g of pure (more than 98%) glycyrrhizinic acid and 36 g of ferrum reductum are stirred with 200 ml of lukewarm water.

The mixture is kept for 3 days with occasional stirring. After 3 days the pH value is measured and eventually corrected to 5.5 ± 0.2, 2800 ml of water is added and the mixture is kept for another 3 days with occasional stirring. After settling of insolubles, the liquid is siphoned off and filtered.

The insoluble material is stirred with 500 ml water and after settling of insolubles the liquid is siphoned, filtered and added to the first filtrate.

The filtrate is evaporated at a temperature of 75°C at diminished air pressure to produce a syrupy liquid which is further dried in a vacuum box at 75°C. The product is a solid cake which is crushed and powdered and kept in a well closed bottle.

Infrared analysis of the products of Examples 1 and 2 and of a solution of iron glycyrrhizinate show that the characteristics peaks of iron glycyrrhizinate are present in all the products.

EXAMPLE 3

The process of Example 1 was repeated except that evaporation in vessel V was conducted under vacuum at a temperature of around 50°C until a syrup having a moisture content of around 30% remained. This was then baked to a dry solid by heating at 110°C for 24 hours. The yield and product was similar to that of Example 1. Analysis of its solubility by the method described above showed that it contained 31.4% by weight insoluble materials and 1.63% by weight soluble glycyrrhizinic moieties measured as the acid.

EXAMPLE 4

The process of Example 3 was repeated except that the baking was conducted at different temperatures for various durations. When baking was at 70°C for 120 hours the product contained 18.7% insoluble materials and 1.51% glycyrrhizinic moieties, measured as acid. When baking was at 140°C for 24 hours the product contained 32.3% insoluble materials.

EXAMPLE 5

The process of Example 1 may be repeated using reduced aluminium in place of ferrum reductum.

EXAMPLE 6

Tablets were prepared by mixing together in a standard tabletting operation 150 mg of the product of Example 1, 25 mg magnesium oxide, 125 mg magnesium trisilicate and 150 mg lactose and conventional excipients.

EXAMPLE 7

Suppositories may be prepared in the form of gelatin rectal capsules each containing 200 mg of the product of Example 1.

EXAMPLE 8

An ointment for topical application for the treatment of rheumatic and skin diseases may contain 2% of the product of Example 1 in a lanoline base.

The solubility and analysis of the products of Examples 1 and 2 and of the composition of Example 6 has been determined and the results are set out in Table 1.

TABLE I

|  | Example 1 | Example 2 | Example 6 |
|---|---|---|---|
| Solubility in water | 1.9 | 0.39 | 1.1 |
| ethanol | 0.13 | 0.16 | 0.22 |
| chloroform | 0.13 | 0.17 | 0.16 |
| benzene | 0.23 | 0.35 | 0.35 |
| ether | 0.13 | 0.40 | 0.21 |
| Iron content | 0.98% | 5.83% | 0.29% |
| glycyrrhizinic acid | 20% | 90% | 5% |
| sulphated ash | 15.9% | 10.1% | 45% |
| moisture | 10.7% | 28% | 9.1% |
| arsenic | less than 2 ppm | less than 2 ppm | less than 2 ppm |
| lead | less than 5 ppm | less than 5 ppm | less than 5 ppm |

A suitable daily dosage of the sparingly soluble iron or aluminium glycyrrhizinate derived from liquorice for the healing of gastroduodenal ulcer is from 100 to 2000, preferably 600 to 1200, mg per day or approximately 10 to 400, preferably 60 to 240, mg per day of glycyrrizinic moieties. Administration is conducted usually for about 4 weeks for gastric ulcer and for about 6 weeks for duodenal ulcer to heal radiologically. It is desirable to continue the treatment for a considerable period, for example 6 weeks, after radiological healing of the ulcer has occurred since this minimizes the risk of reoccurrence of the ulcer by allowing every trace of hyperaemia (a symptom which accompanies all inflammation) to be eliminated. Hyperaemia could, of course, be a harbinger of inflammation and its presence on the healed site of the old wound surface might well be a cause for reoccurrence. The very fact that the tablets described in Example 6 can be administered for uninterrupted long periods without causing any undesirable side effects is an important feature in the longer term prevention of ulcer reoccurrence.

The dosage prior to radiological healing is usually higher than the dosage after. For example prior to radiological healing the daily dosage may be 1200 mg of the product of Example 1 while subsequent to radiological healing it would be 600 mg of the product of Example 1. For example a useful treatment comprises the administration of eight tablets as described in Example 6 per day until radiological healing has occurred and four tablets per day for 6 weeks thereafter.

In order to verify its pharmaceutical activity a double blind trial of the product of Example 6 was conducted against a placebo on 26 patients with radiologically confirmed gastric or duodenal ulcers. The patients were divided into two equal groups A and B, each receiving eight tablets daily of the product of Example 6 or a placebo until radiological healing and then three tablets daily during the following 6 weeks. Patients still reporting subjective symptoms after ten days double blind treatment were transferred for a completely new trial to a third group C and treated with the product of Example 6 only.

After completion of the trial the code was broken and revealed the group A received placebo only and group B had received the product of the invention. Seven patients in group A were transferred to group C after treatment for 10 days with the placebo had not cured the subjective symptoms. The results are summarized in Table 2 from which it will be seen that all 20 patients who received the product of Example 6 experienced radiological healing, whereas of the 13 receiving the placebo only 6 recovered radiologically.

In addition to the marked therapeutic effect of the product undesirable side effects, such as those that have been observed previously when using liquorice or gta derivatives thereof, were entirely absent. Thus oedema, headache, hypertension, dyspnoea, salt and water retention and potassium excretion did not occur.

TABLE II

| Group | Ulcer type | Total Number of Patients | Successful Radiological Healing |
|---|---|---|---|
| A | Gastric | 3 | 2 |
|  | Duodenal | 10 | 4 |
| B | Gastric | 3 | 3 |
|  | Duodenal related to pyloric ulcer | 2 | 2 |
|  | Other Duodenal | 8 | 8 |
| C | Gastric | 1 | 1 |
|  | Duodenal | 6 | 6 |

Toxicity tests, e.g., on mice, give satisfactory results.

I claim:

1. A sparingly soluble product containing a metal glycyrrhizinate selected from the group consisting of iron glycyrrhizinate and aluminium glycyrrhizinate in which the amount of glycyrrhizinic moieties is at least 5% by weight and at least two thirds of the glycyrrhizinic moieties are insoluble in water, the glycyrrhizinic moiety weight being calculated as acid, said product being obtained by heating an aqueous solution of the corresponding water-soluble metal glycyrrhizinate at a temperature of at least 70°C. for at least 6 hours.

2. A product according to claim 1 in which 1 to 33% by weight of total glycyrrhizinic moieties are soluble and 67 to 99% by weight are insoluble the weights being calculated as acid.

3. A product according to claim 1 containing at least 10% by weight total glycyrrhizinic moieties, the weight being calculated as acid, at least four fifths by weight of the moieties being insoluble, the remainder being soluble.

4. A product according to claim 1 containing at least 10% by weight total glycyrrhizinic moieties and in which from 5 to 15% by weight of the total glycyrrhizinic moieties are soluble adn 85 to 95% by weight are insoluble the weights being calculated as acid.

5. A product according to claim 1 containing from 1.5 to 2.5% by weight soluble glycyrrhizinic moieties and 25 to 35% insoluble materials and which contains at least 10% by weight total glycyrrhizinic moieties, at least four fifths by weight of these being insoluble.

6. A product according to claim 1 containing from 1.5 to 2% soluble glycyrrhizinic moieties and 30 to 33% insoluble materials and which contains at least 10% by weight total glycyrrhizinic moieties, at least four fifths by weight of these being insoluble.

* * * * *